(12) United States Patent
Lin et al.

(10) Patent No.: US 9,186,423 B1
(45) Date of Patent: Nov. 17, 2015

(54) COMPOUND OF RADIOCONTRAST AGENT FOR TAU PROTEIN

(71) Applicant: Institute of Nuclear Energy Research, Atomic Energy Council, Executive Yuan, R.O.C., Taoyuan County (TW)

(72) Inventors: Wuu-Jyh Lin, Taoyuan County (TW); Shiou-Shiow Farn, Taoyuan County (TW); Yean-Hung Tu, Taoyuan County (TW); Li-Yuan Huang, Taoyuan County (TW); Dow-Che Chen, Taoyuan County (TW); Kuo-Yuan Chu, Taoyuan County (TW); Mao-Hsung Chang, Taoyuan County (TW); Ting-Shien Duh, Taoyuan County (TW); Jenn-Tzong Chen, Taoyuan County (TW); Chyng-Yann Shiue, Taoyuan County (TW)

(73) Assignee: INSTITUTE OF NUCLEAR ENERGY RESEARCH, ATOMIC ENERGY COUNCIL, Executive Yuan, R.O.C., Lungtan, Taoyuan (TW)

( * ) Notice: Subject to any disclaimer, the term of this patent is extended or adjusted under 35 U.S.C. 154(b) by 0 days.

(21) Appl. No.: 14/492,174

(22) Filed: Sep. 22, 2014

(51) Int. Cl.
*C07C 211/00* (2006.01)
*A61K 51/04* (2006.01)

(52) U.S. Cl.
CPC ..................... *A61K 51/04* (2013.01)

(58) Field of Classification Search
None
See application file for complete search history.

(56) References Cited

U.S. PATENT DOCUMENTS

2005/0232387 A1* 10/2005 Padgett .............. A61K 51/0491 376/194

* cited by examiner

*Primary Examiner* — Rosalynd Keys
*Assistant Examiner* — Jennifer C Sawyer
(74) *Attorney, Agent, or Firm* — Jackson IPG PLLC; Demian K. Jackson

(57) ABSTRACT

A radiocontrast agent for tau protein is provided. The agent is selectively and strongly bound to tau protein and its tangle found in brain diseases like Alzheimer's disease (AD). The agent is especially suitable to be used in PET imaging for brain diseases. Or, the agent can be used to inhibit tau protein overexpressive and, thus, stop the proceeding of brain disease.

5 Claims, 1 Drawing Sheet

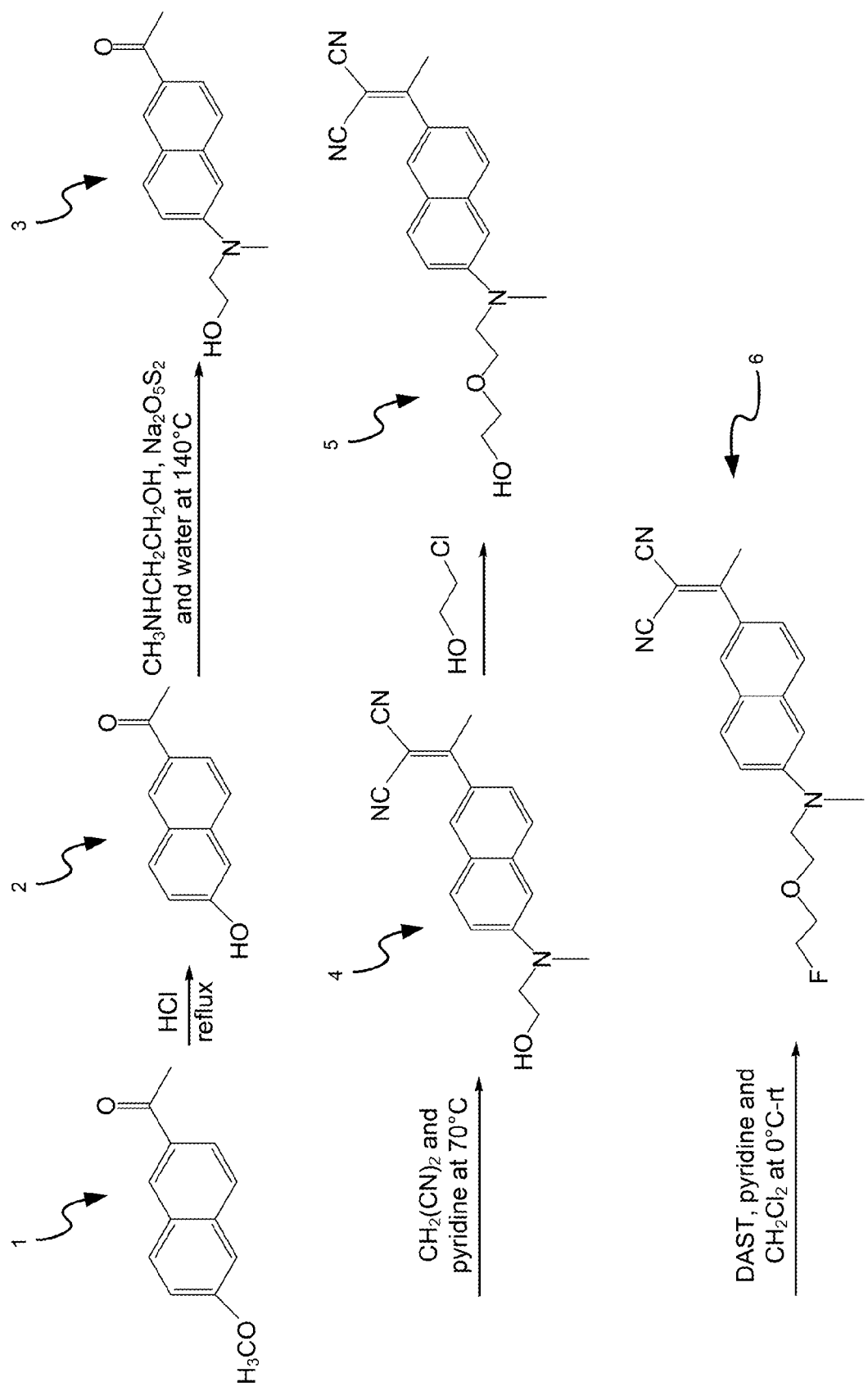

COMPOUND OF RADIOCONTRAST AGENT FOR TAU PROTEIN

FIELD OF THE INVENTION

The present invention relates to a radiocontrast agent; more particularly, relates to a compound of radiocontrast agent selectively and strongly binding to β-amyloid protein (Aβ protein), where the compound is suitable for PET imaging for showing plaques having the specific Aβ protein in a patient of brain disease, like Alzheimer's disease (AD); and, the compound is also suitable to be used in a treatment drug for brain disease therapy by inhibiting the plaques having Aβ protein and, thus, further stopping the proceeding of brain disease. Besides, this compound can also be a potential brain disease imaging agent such as brain tumor due to its biochemical properties and the similarity between tau protein and tumor suppressor gene.

BACKGROUND OF THE INVENTION

AD is a drifting brain degenerative disease, also known as a degenerative senile dementia, which is one of the most common and incurable dementia. AD occurs in the elderly, where older people have higher opportunities to get sick and people older than 85 years old have a 30~35% prevalence rate. This progressive disease has its main clinical manifestations of degradation in three areas, including cognition, behavior and mental state. It has a special change in neuropathology, where some phenomena can be seen with naked eyes, like atrophy on appearance of cerebral cortex, widening of brain's back groove, and ventricular enlargement. Among them, most important pathological diagnostic indicators for AD are neurofibrillary tangles (NFT) and senile plaques (SP), which are widely distributed in neocortex. NFT is a result of windings of paired helical filaments of abnormal phosphorylated tau protein, which causes the formation of neurofibrillary tangles inside nerve cells. SPs are compositions of amyloid, where fibril deposits of Aβ protein are formed outside of nerve cells.

In recent researches, many small round precipitations or plaques are found in brains of AD patients. These spider web-like tangles of proteins are Aβ protein, which has become the focus on discussing AD mechanisms and treatments.

In prior studies, biological flags of AD can be divided into three categories, namely styrlbenzenes, like X-34, ISB, BSB, SB13 and IMSB; aminonaphthalene, like FDDNP and FENE; and thioflavin-S(TF-S), like 6-OH-BTA-1, TZDM and IMPY. Therein, FDDNP of aminonaphthalene is labeled with radioisotope fluorine(F)-18 to become F-18-FDDNP to be used as a contrast agent for positron emission tomography (PET).

In recent years, an increasing number of radiopharmaceuticals for Aβ protein plaques in positron CT scan have been developed and proven the feasibility of application on human body imaging. The use of the radiopharmaceuticals for tracing Aβ protein plaques can effectively assist in diagnosis of AD and related brain diseases, and can be used to evaluate effectiveness of the treatment drug for reducing accumulation of Aβ protein plaque in brain. But, a radiocontrast agent selectively and strongly bound to Aβ protein plaques to be used in PET imaging for AD and related brain diseases; or, to inhibit Aβ protein plaques for stopping the proceeding of AD and related brain disease, is still not found.

Hence, the prior arts do not fulfill all users' requests on actual use.

SUMMARY OF THE INVENTION

The main purpose of the present invention is to provide a tau-protein radiocontrast agent strongly and selectively binding to tau tangle.

Another purpose of this invention is to provide a nuclear diagnostic drug for tau protein used in PET imaging for brain diseases.

Another purpose of the present invention to provide a treatment drug for AD therapy by inhibiting tau protein tangle formation and, thus, further stopping the proceeding of brain disease.

To achieve the above purposes, the present invention is a compound of radiocontrast agent for tau protein, where the compound has the following structural formula:

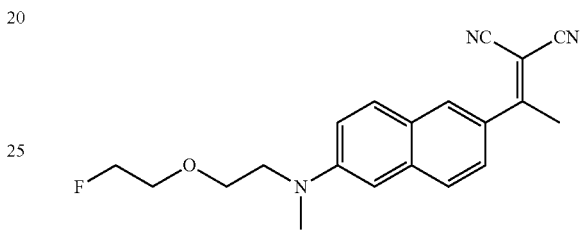

and F is a radioactive element with labeling function or a non-radioactive element without labeling function.

Accordingly, a novel compound of radiocontrast agent for tau protein is obtained.

BRIEF DESCRIPTION OF THE DRAWINGS

The present invention will be better understood from the following detailed description of the preferred embodiment according to the present invention, taken in conjunction with the accompanying drawing, in which FIG. 1 is the view showing the flow of fabricating the preferred embodiment according to the present invention.

DESCRIPTION OF THE PREFERRED EMBODIMENT

The following description of the preferred embodiment is provided to understand the features and the structures of the present invention.

Please refer to FIG. 1, which is a view showing a flow of fabricating a preferred embodiment according to the present invention. As shown in the FIGURE, the present invention is a compound of radiocontrast agent for tau protein, having the following formula:

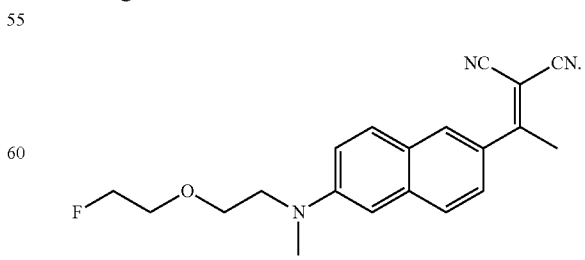

For diagnosis, the compound preferably has a radioactive element with labeling function, like fluorine(F)-18, to be used as a contrast agent in PET imaging for brain diseases and neurodegenerative disorders, like Alzheimer's disease (AD), related to tau protein and β-amyloid protein (Aβ protein), or brain tumor, also related to tau protein or glutamate overexpression.

For treatment, the compound preferably has a nonradioactive element without labeling function, like F-19, to be used as a cranial nerve drug of fluorine standard for AD, neurodegenerative disorders or diseases and conditions related to tau protein and Aβ protein.

The present invention also provides a method for fabricating the compound of radiocontrast agent for tau protein:

[Step 1] Fabrication of 2-Acetyl-6-hydroxynaphthalene

At first, 2-acetyl-6-methoxynaphthalene 1 (hereinafter referred to as first compound 1) is obtained as a starting reactant. 1.48 grams (g) (7.3 milli-moles (mmol)) of the first compound 1 is put in 500 mL of concentrated hydrochloric acid to be heated with reflux for 2 hours (hr). After being hot-filtered, the filtered solution is cooled down for extraction with dichloromethane (2×200 milli-liters (mL)). After discarding hydrochloric acid, 200 mL of water is used to wash out an organic phase. After being dried with anhydrous sodium sulfate, the organic phase is evaporated and dried under a reduced pressure to obtain an off-white solid product of 2-Acetyl-6-hydroxynaphthalene 2 (hereinafter referred to as second compound 2), which has a weight of 1.3 g and a yield of 95.7%.

[Step 2] Fabrication of 2-Acetyl-6-[(2-hydroxyethyl)methylamino]naphthalene 0.4 g (2.1 mmol) of the second compound 2 is obtained to be mixed with 1.8 g (24.0 mmol) of 2-methylaminoethanol ($CH_3NHCH_2CH_2OH$), 2.0 g (19.2 mmol) of sodium bisulfite ($Na_2O_5S_2$) and 4 mL of water to be heated to 140 celsius degrees (° C.) with vigorous stirring and refluxed for 76 hrs. After cooling, 50 mL of dichloromethane is added for phase separation after sufficient stirring. Therein, after being dried with anhydrous sodium sulfate, an organic phase is concentrated under reduced pressure and separated and purified by liquid chromatography ($SiO_2$, $EtOAc:CH_2Cl_2=1:3$), with 0.15 g (0.81 mmol) of the second compound 2 recycled. Thus, a solid product, 2-acetyl-6-[(2-hydroxyethyl)methylamino]naphthalene 3 (hereinafter referred to as third compound 3), is obtained, which has a weight of 0.276 g and a yield of 88.0%.

[Step 3] Fabrication of 2-(1,1-dicyanopropen-2-yl)-6-[(2-hydroxyethyl)methylamino]naphthalene 4

0.51 g (2.1 mmol) of the third compound 3 is dissolved in 3 mL of dry pyridine to be added with 0.63 g (8.3 mmol) of malononitrile ($CH_2(CN)_2$). Reaction is processed under nitrogen to be heated at 70° C. with stirring for 4 hrs. After cooling, 50 mL of ether is added with sufficient stirring, where the part insoluble to ether is abandoned. The ether solution is washed with 50 mL of water. After being dried with anhydrous sodium sulfate and concentrated under reduced pressure, an organic phase is separated and purified by liquid chromatography ($SiO_2$, $CHCl_3:EtOAc=1:1$). Thus, a red solid product, 2-(1,1-dicyanopropen-2-yl)-6-[(2-hydroxyethyl)methylamino]naphthalene 4 (hereinafter referred to as fourth compound 4), is obtained, which has a weight of 0.46 g and a yield of 75.3%.

[Step 4] Fabrication of 2-(1,1-dicyanopropen-2-yl)-6-{[2-(2-hydroxy-ethoxy)-ethyl]methylamino}naphthalene 5

0.40 g (1.4 mmol) of the fourth compound 4 is obtained to be dissolved in 8 mL of anhydrous acetonitrile. 0.35 g (4.3 mmol) of 2-chloro-ethanol is added to be heated with stirring at 80° C. for 17 hrs. After cooling, extraction is processed with dichloromethane. After being dried with anhydrous sodium sulfate, an organic phase is concentrated under reduced pressure to be separated and purified by liquid chromatography ($SiO_2$, $CHCl_3:EtOAc=1:1$). Thus, a product, 2-(1,1-dicyanopropen-2-yl)-6-{[2-(2-hydroxy-ethoxy)-ethyl]methylamino}naphthalene 5 (hereinafter referred to as fifth compound 5), is obtained, which has a weight of 0.29 g and a yield of 60.0%.

[Step 5] Fabrication of 2-(1,1-dicyanopropen-2-yl)-6-{[2-(2-fluoro-ethoxy)-ethyl]methylamino}naphthalene 6

0.20 g (0.6 mmol) of the fifth compound 5 is obtained to be dissolved in 10 mL of anhydrous methylene chloride. 0.16 mL (1.2 mmol) of (diethylamino)sulfur trifluoride (DAST) is added at 0° C. for reaction at a room temperature for 16 hrs. After the reaction is completed, extraction is processed with water and dichloromethane. An organic phase is collected with water removed by sodium sulfate and is concentrated under reduced pressure to be separated and purified by liquid chromatography. Thus, the final product 6,2-(1,1-dicyanopropen-2-yl)-6-{[2-(2-fluoro-ethoxy)-ethyl]methylamino}naphthalene, is obtained, which has a weight of 0.12 g and a yield of 60.0%.

Thus, a novel compound of radiocontrast agent for tau protein is obtained.

To sum up, the present invention is a compound of radiocontrast agent for tau protein, where a tau-protein radiocontrast agent strongly and selectively binding to Aβ protein plaques is provided; the radiocontrast agent is used as a nuclear diagnostic drugs for Aβ protein plaques in PET imaging for brain diseases like AD; or, the radiocontrast agent is used as a treatment drug for brain disease therapy by inhibiting Aβ protein plaques and, thus, further stopping the proceeding of brain disease.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A compound of radiocontrast agent for tau protein, comprising a structural formula:

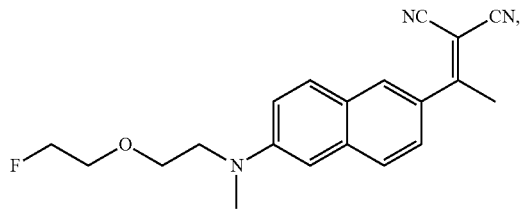

wherein, F is an element selected from a group consisting of a radioactive element with labeling function and a non-radioactive element without labeling function.

2. The compound according to claim 1, wherein said radioactive element is F-18.

3. The compound according to claim 2,
wherein the compound having said radioactive element is a drug used in diagnosis with PET imaging for brain diseases and neurodegenerative disorders or other disease.

4. The compound according to claim 1,
wherein said non-radioactive element is F-19.

5. The compound according to claim 4,
wherein the compound having said non-radioactive element is a cranial nerve drug of fluorine standard used in treatment for brain diseases and neurodegenerative disorders related to tau protein and Aβ protein.

* * * * *